United States Patent [19]

Rucker

[11] 4,302,577

[45] Nov. 24, 1981

[54] PROCESS FOR PREPARING CSA OR CSC

[75] Inventor: Perry G. Rucker, Los Angeles, Calif.

[73] Assignee: Biomed Research Inc., Los Angeles, Calif.

[21] Appl. No.: 118,211

[22] Filed: Feb. 4, 1980

Related U.S. Application Data

[63] Continuation-in-part of Ser. No. 82,045, Oct. 5, 1979, abandoned.

[51] Int. Cl.$^3$ ............................................. C07H 11/00
[52] U.S. Cl. ..................................... 536/118; 435/267
[58] Field of Search ................ 424/180; 435/267, 272, 435/274, 68, 69, 99, 276; 536/118

[56] References Cited

U.S. PATENT DOCUMENTS

| | | | |
|---|---|---|---|
| 3,016,331 | 1/1962 | Toccaceli ........................ | 435/274 X |
| 3,342,683 | 9/1967 | Hashimoto et al. ............ | 435/274 X |
| 3,862,003 | 1/1975 | Okuyama et al. .................... | 435/274 |
| 3,895,106 | 7/1975 | Morrison .............................. | 424/180 |
| 3,895,107 | 7/1975 | Morrison .............................. | 424/180 |

*Primary Examiner*—Robert J. Warden
*Attorney, Agent, or Firm*—Joseph E. Mueth

[57] ABSTRACT

An improved process or method for the preparation of pharmaceutical grade biologically and physiologically "active" chondroitin sulfate, predominantly chondroitin sulfate A, chondroitin sulfate C, and mixtures thereof from source material comprising forming a solution from the source material containing said "active" material, adding thereto a complexing agent to form a precipitate which is a water insoluble complex of the active material and the complexing agent, and breaking said complex to recover the pharmaceutical grade "active" material.

10 Claims, No Drawings

PROCESS FOR PREPARING CSA OR CSC

BACKGROUND OF THE INVENTION

This is a continuation-in-part of patent application Ser. No. 82,045, filed Oct. 5, 1979 now abandoned.

As described in U.S. Pat. No. 3,895,106 and U.S. Pat. No. 3,895,107, there exists the method of treatment for inhibiting the development of atherosclerotic lesions in animals of the mammalian species, promoting the development of collateral circulation in regions of the heart supplied by the branches of coronary arteries, and inhibiting the occurrence of cardiac episodes including myocardial infarctions, acute coronary insufficiency with acute myocardial ischemia in human subjects with ischemic heart disease, which comprises the essentially regular and prolonged oral administration to mammals of an effective amount of a biologically and physiologically "active" chondroitin sulfate A, "active" chondroitin sulfate C, or mixtures thereof, said activity being manifested by at least an 80% prolongation of plasma thrombus-formation time 6 to 12 hours after administration in rabbits as described in the Chandler loop method.

In a recently completed study comparing oral chondroitin sulphate with placebo in the prevention of post-operative deep vein thrombosis, it was concluded that oral CSA decreased the incidence of post-operative DVT as detected by the radioactive fibrinogen test in general surgical patients and in gynaecological patients. Furthermore, that study revealed no evident complications from the administration of the drug.

According to these patents, the "active" CSA and CSC is obtained by digesting and solubilizing the ground and defatted source material such as bovine trachea and shark cartilage by prolonged exposure to papain activated by cystein hydrochloride and disodium versenate. To the solution containing various extraneous material along with the desired "active" CSA and/or CSC is then added two volumes of acetone which precipitates the desired CSA and/or CSC.

The foregoing procedure has several disadvantages in practice. Precipitation is not complete unless large volumes of acetone are used. The use of large volumes of acetone is inconvenient, dangerous and cumbersome, and even at best, at least some of the desired active CSA and/or CSC is not precipitated and is lost. The loss becomes greater as the relative volume of the acetone is cut back to facilitate handling.

I have discovered that these problems and difficulties can be almost entirely eliminated by the use of certain complexing agents in lieu of acetone. More particularly, I have found that complexing agents such as quaternary ammonium compounds selectively form water-insoluble complexes with "active" CSA and CSC, causing an essentially quantitative precipitation of the CSA and CSC, and concomitantly, leaving all of the other unwanted materials behind in the supernatant.

According to my invention, it is no longer necessary to handle large volumes of acetone and similar materials. Moreover, it is quite surprising that these complexes form, and that they form selectively with the "active" CSA and/or CSC. While not bound by any theory, it is believed that the complexing agents and the "active" CSA and/or CSC are oppositely charged and hence are attracted to each other to form some type of bond. In any event, the effect of the bond is to cause total precipitation. The bond can subsequently be readily interrupted by a base such as sodium hydroxide and/or hypertonic saline to yield the free "active" CSA and/or CSC. I believe that this improved method represents a significant advance in the preparation of this important drug.

SUMMARY OF THE INVENTION

Briefly, this invention comprises an improved process or method for the preparation of pharmaceutical grade biologically and physiologically "active" chondroitin sulfate, predominantly chondroitin sulfate A, chondroitin sulfate C, and mixtures thereof from source material comprising forming a solution from the source material containing said "active" material, adding thereto a complexing agent to form a precipitate which is a water insoluble complex of the active material and the complexing agent, and breaking said complex to recover the pharmaceutical grade "active" material.

It is an object of this invention to provide an improved method for the preparation of "active" CSA and/or CSC.

It is a further object of my invention to provide a safer, and more convenient means for recovering and isolating "active" CSA and/or CSC.

Still further, it is an object of my invention to provide for the isolation of "active" CSA and/or CSC in a virtual quantitative basis.

In another aspect, it is an object of the invention to prepare a novel complex of CSA and/or CSC which is formed as a precipitate in aqueous solution and can be readily interrupted upon recovery of the precipitate to yield the free "active" CSA and/or CSC.

These and other objects and advantages of this invention will be apparent from the detailed description which follows.

DESCRIPTION OF THE PREFERRED EMBODIMENTS

The present invention is applicable to "active" CSA and/or CSC from all of the usual sources such as bovine trachea, whale and shark trachea, porcine trachea, and in fact, to mammalian tissues generally. The initial treatment of the crude material from the animal or fish, as supplied by packing houses and the like, is to trim away the fat and to chop or grind the tracheal and or other tissues.

The finely divided source material is then digested using pepsin, papain or other proteolitic enzymes to remove proteins. Concurrently or sequentially, the protein removal and solubilization of the CSA and CSC can be accomplished with the benefit of strong bases such as sodium hydroxide and potassium hydroxide. Strong hydrochloric acid is also effective for this purpose.

In any case, an aqueous solution of the CSA and/or CSC is obtained. This solution contains many other unwanted and, in many cases, detrimental components, resulting from the chemical breakdown of the source material, and it is the main purpose of this invention to, separate and remove the "active" CSA and/or CSC from these unwanted or detrimental components.

In accordance with this invention a novel and unique insoluble complex of CSA and/or CSC and complexing agents is formed from aqueous solution. The complexing agents are, for example cetyl pyridinium chloride sold as "Barquat" by Hexcel Specialty Chemicals, or n-alkyl dimethyl benzyl ammonium chloride having the formula:

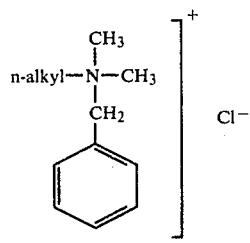

wherein the alkyl group is predominantly $C_{12}$ to $C_{18}$. Such materials are available as "Marqual" from Mason Chemical Company.

Another and equally useful complexing agent for "active" CSA and/or CSC are various anion exchange resins such as "Dowex 1-X" by Dow Chemical Company. These materials are further described in U.S. Pat. No. 2,591,573 and U.S. Pat. No. 2,591,574. In general, these resins are crosslinked benzene-divinylbenzene copolymers containing lower alkyl quaternary amine groups.

After precipitation and collection of the complex the complex can be broken or interrupted by contact with mild base and/or hypertonic saline to yield the freed "active" CSA and/or CSC. This material is directly useful in a capsule, tablet, etc., for oral administration to humans, particularly as an anti-thrombic agent. The dosage levels are as described in the patents initially discussed hereinabove. If it is desired to present the drug in parenteral form, the freed "active" CSA and CSC can be further treated with oxidizing agents such as potassium permanganate to eliminate any traces of extraneous oxidizable components.

The following example is for purposes of illustration and is not intended to be limiting in any way. In the examples, the parts and percentages are by weight unless otherwise indicated.

EXAMPLE

One hundred pounds of trimmed bovine trachea was chopped into 1 inch square segments and added to about 50 gallons of deionized water in a tank. The pH was adjusted to about 4.5 by addition of approximately 400 ml of glacial acetic acid. The resulting suspension was agitated while the contents of the tank was raised to about 50° C. One and one-quarter pounds of pepsin was added and the agitation continued for 30 minutes. Another 50 gallons of de-ionized water was added to the tank and mild stirring continued for 12 hours at 50° C. until the tracheal cartilage is freed of connective tissue. The temperature of the suspension is then raised to 80° C. and a fat layer formed on the top of the liquid. The digestion liquor was drained off through a basket centrifuge and discarded.

The remaining solids were twice washed with 50 gallons of hot water (60°–80° C.). A sodium hydroxide solution was prepared by adding 1.5 lbs. of NaOH to 5 gallons of de-ionized water in a tank. The twice washed solids were added to the sodium hydroxide solution, and the volume adjusted with de-ionized water to 12 gallons and the pH to 9–10. The contents of the tank was agitated for 12 hours at 37° C. The pH was then adjusted to 6.5 with glacial acetic acid. The liquid was heated to boiling and then permitted to cool. The liquid was filtered through a basket centrifuge and the filtrate collected and retained. To the retained filtrate was added 1.5 pounds of cetyl pyridinium chloride followed by stirring for 30 minutes. The liquid was allowed to stand for 16 hours. A precipitate form. The supernatant was decanted and the precipitate collected by continuous centrifugation in a Sharples centrifuge. The collected precipitate was in 5 gallons of 0.5 N sodium hydroxide. Ten gallons of methanol was added and allowed to stand for 12 hours at room temperature. The precipitate formed was again collected by continuous centrifugation and washed with 5 gallons of methanol. The precipitate was dissolved in two gallons distilled water, the pH adjusted to 7.0 with glacial acetic acid and ¼ pound of sodium chloride was added, followed by stirring. Four gallons of methanol was added and agitation was carried out for 15 minutes. After standing for 12 hours at room temperature, a precipitate had formed which was collected by centrifugation. The precipitate was dried under vacuum. Analysis showed the precipitate to be essentially CSA. The material manifested a prolongation of plasma thrombus formation time 6 to 12 hours after administration in rabbits as described by the Chandler loop method of over 80%.

In the following study, all subjects had clinically evident Occlusive Arterial Peripheral Vascular Disease presenting with intermittent Claudication and signs of impaired arterial blood flow to one or both lower limbs. In all subjects admitted the clinical status and disease activity had remained relatively stable during the preceding six months. None of the subjects had received any anti-coagulant or thrombolytic therapy during the preceding six months. Furthermore subjects in receipt of vasodilator drugs had remained in receipt of a constant dosage of such during the preceding six to eight month period.

Subjects with other conditions which restricted their activity such as cardiac disease, were excluded, as were subjects with Diabetes Mellitus, and subjects who had undergone vascular surgery abdominal aorta, iliac arteries, superficial and deep femoral arteries and the terminal branches of such within the lower limbs.

At initial assessment the following clinical data were obtained: age; weight; height; smoking habits; presence of varicose veins; severity of calf pain both at rest and upon walking. Patients were stratified for age, sex and cigarette-smoking status and were randomly allocated to a control group (placebo) or active treatment group (the "active" CSA prepared as per the foregoing Example).

The active test substance was in the form of tablets containing 500 mg of "active" CSA. Placebo tablets were identical in shape, colour and consistency as the active tablets. Following stratification subjects were randomly allocated to receive either the active-substance or placebo according to the following regimen:

For the first five days of treatment: 12 tablets per day in four equal doses of three tablets.

From the sixth to the tenth day of treatment: eight tablets per day in four equal doses of two tablets.

From the eleventh day of treatment for a subsequent period of thirteen weeks: four tablets per day in four equal doses.

The duration of treatment was fourteen weeks, the patients being assessed every two weeks for the first six weeks and monthly thereafter during the treatment period of the study. However, prior to the treatment period assessments were undertaken according to the following schedule:

The first pre-treatment assessment took place six weeks prior to admission to the treatment period and subjects were further assessed at intervals of two weeks in the period prior to entry to the treatment phase.

At all assessments, the patient's general condition was recorded. The clinical severity of the claudication and the condition of the skin were classified as mild, moderate, or severe. Each patient's individual maximum walking distance was accurately recorded in meters and any concomittant symptoms were noted.

At each assessment the following further clinical and laboratory measures were undertaken:

1. Segmental Plethysomography of one or both lower limbs.
2. Micromanometric measurement of foot arterial blood pressure.
3. Timing of the onset of calf pain at the standard walking rate.
4. The following subjective measures of clinical response:

Number of attacks of calf pain on walking during the day preceding the assessment-visit.

Severity of calf pain measured on a visual analogue scale.

Number of episodes of calf-pain at rest during the week preceding the assessment-visit.

Assessment of change based on a visual analogue scale.

Type and frequency of volunteered side effects.

5. Laboratory Measures:

(a) Haematology: Haemoglobin concentration, PCV, MCHC, WBC Count and Differential Count, platelet count, reticulocyte count, and ESR.

(b) Plasma fasting levels of fibrinogen.

(c) Serum fasting levels of cholesterol, lipoproteins, and triglycerides.

(d) Blood coagulation mechanisms: plasma thrombin clotting time; Euglobulin lysis time and platelet aggregation time.

Forty-one patients were included in the study, that is twenty-two in the active CSA, and nineteen in the control placebo Group. All the patients had bilateral disease.

Clinical, laboratory, and coagulation data on the forty-one patients admitted to the trial are shown in Table 1.

TABLE 1

CLINICAL AND LABORATORY DATA IN TWO GROUPS OF PATIENTS ON ADMISSION TO STUDY: MEANS ± S.E.M.

|  | "CSA" Group | Placebo Group |
|---|---|---|
| Number of Cases | 22 | 19 |
| Age (years) | 62 ± 1.09 | 61 ± 0.94 |
| Cigarette Smokers (% of group) | 77.3 | 73.7 |
| % Overweight for height | 31.8 | 36.8 |
| Walking distance (metres) | 55.4 ± 3.9 | 55.9 ± 4.7 |
| Calf pain at rest (rate per week) | 11.8 ± 1.9 | 11.4 ± 2.0 |
| Calf pain (Visual Analogue/mms) | 45.6 ± 4.5 | 50.1 ± 5.7 |
| Fibrinogen (g/l) | 3.49 ± 0.16 | 3.37 ± 0.13 |
| Plasma Thrombin Clotting Time (% Normal) | 101 ± 1.52 | 103 ± 1.88 |
| Euglobulin Lysis Time (mins) | 327 ± 5.23 | 330 ± 4.24 |
| Platelet Aggregation Time (secs) | 639 ± 3.2 | 641 ± 4.2 |
| Cephalin Time (secs) | 40.1 ± 0.34 | 41.3 ± 0.41 |
| Cholesterol (mg/dl) | 295.1 ± 2.8 | 297.3 ± 3.48 |
| 'S' Particles (mg/dl) | 535.7 ± 6.1 | 539.4 ± 5.6 |
| Maximum Calf blood flow (ml/100ml tissue/minute) | 20.8 ± 1.91 | 19.4 ± 1.8 |

The difference between the groups are not significant at the 0.05 level.

The two groups were comparable in age distribution, sex ratio, cigarette-smoking status, and in their scores on subjective and objective measures of clinical response.

The improvement in walking distance exhibited by each of the groups is given in Table 2.

TABLE 2

IMPROVEMENT IN WALKING DISTANCE

| THERAPY: | No. PATIENTS: | PRETRIAL: | WALKING DISTANCE IN METERS (MEAN ± SEM): | | | | | |
|---|---|---|---|---|---|---|---|---|
| | | | WEEK 0: | WEEK 2: | WEEK 4: | WEEK 6: | WEEK 10: | WEEK 14: |
| "CSA" | 22 | 55.4 ± 3.9 | 52.6 ± 4.1 | 53.1 ± 3.8 | 78.0 ± 5.7* | 81.2 ± 4.9* | 86.7 ± 5.1* | 89.3 ± 6.2* |
| PLACEBO | 19 | 55.9 ±4.7 | 53.8 ± 4.3 | 54.5 ± 4.9 | 49.3 ± 4.5* | 49.6 ± 5.0* | 50.3 ± 4.9 | 48.7 ± 5.1 |

*Significant Improvement in "CSA" groups; $t_{ind} = 3.98$; $p<0.01$

| THERAPY | TOTAL CASES | NUMBER OF PATIENTS IMPROVED IN RELATION TO WALKING DISTANCE | | | | | |
|---|---|---|---|---|---|---|---|
| | | WEEK 0: | WEEK 2: | WEEK 4: | WEEK 6: | WEEK 10: | WEEK 14: |
| "CSA" | 22 | 2(9.1%) | 6(27.3%) | 11(50.0%) | 14(63.6%) | 15(68.2%) | 14(63.6%) |
| PLACEBO | 19 | 2(10.5%) | 3(15.8%) | 2(10.5%) | 4(21.1%) | 3(15.8%) | 4(21.1%) |

At the fourth week of treatment there was a significant improvement in walking distance exhibited by the group in receipt of chondroitin sodium sulphate ($t_{ind}=3.98$; $P<0.01$). This improvement was sustained throughout the remaining ten weeks of the study. There was no significant improvement in walking distance in the group in receipt of placebo.

In Table 2 are also shown the number of patients improved in relation to walking distance. By arbitrary definition a nonimproved patient exhibited no increase in walking distance or a minimal improvement (e.g. an initial claudication distance of 50 meters improving to 65 meters). "Improved" patients showed a marked increase in walking distance (e.g. 50 meters initially, improving to 80–90 meters). It would appear from the data displayed in Table 2 that the "improved patients" showed an intermediate increase in walking distance at the fourth, sixth, and tenth week of the treatment period indicating any progressive improvement.

In Table 3 are shown the changes in blood flow (maximum calf-flow response) in the two groups of patients.

TABLE 3

Changes in Blood Flow (Maximum Calf-Flow Response) in the Two Groups of Patients PEAK BLOOD FLOW IN CALF (mls/100ml Tissue/minute)

| THERAPY: | PRETRIAL: | WEEK 0: | WEEK 4: | WEEK 10: | WEEK 14: |
|---|---|---|---|---|---|
| "CSA" | 20.8 ± 1.91 | 19.3 ± 1.76 | 27.4 ± 1.56* | 35.6 ± 1.81* | 34.9 ± 1.90* |
| PLACEBO | 19.4 ± 1.82 | 20.4 ± 1.90 | 18.6 ± 1.73 | 21.3 ± 1.52 | 20.1 ± 1.87 |

*SIGNIFICANT INCREASE IN MEAN FLOW IN "CSA" GROUP
$p < 0.01$

It may be seen that at the fourth week of treatment there was a significant increase in mean flow in the chondroitin sodium sulphate group which was also present at week 10 and week 14 of the study.

Subjects' assessment of change in the severity of calf pain as measured by a Visual Analogue Scale are documented in Table 4.

TABLE 4

Subject's Assessments of change in severity of calf pain adopting the 10cm. line-Visual Analogue Scale MEAN ± SD Calf Pain Severity (cms)

| THERAPY: | No. Subjects: | Week 0 | Week 2 | Week 4 | Week 6 | Week 10 | Week 14 |
|---|---|---|---|---|---|---|---|
| "CSA" | 22 | 3.83 ± 1.68 | 4.01 ± 1.77 | 4.16 ± 1.80 | 6.44 ± 1.71 | 5.63 ± 2.44 | 6.10 ± 2.18 |
| PLACEBO | 19 | 3.76 ± 1.57 | 4.27 ± 2.14 | 4.38 ± 1.52 | 4.16 ± 2.03 | 3.94 ± 1.97 | 3.18 ± 1.88 |
| Value of $t_{ind}$: "CSA" Group: Response vs Week 0 | | / | −0.34 | −0.63 | −5.10** | −2.84* | −3.86** |

Significant improvement in "CSA" group only
*$P < 0.01$;
**$P < 0.001$

Only in the "CSA" Group was a significant improvement noted, which first became apparent at week 6 of the treatment period. Laboratory and coagulation data, obtained in the study, in the two treatment groups are given in Table 5.

In the present study the oral administration of "active" CSA was not associated with any significant changes in the plasma thrombin clotting time and platelet aggregation time.

Again it is not possible to delineate the possible modes of action of "active" CSA but the significant reduction in the levels both of plasma fibrinogen and serum cholesterol levels may be of major importance.

It was also decided to undertake a controlled trial to assess the effectiveness of "active" CSA prepared as described hereinabove in the prevention of post-operative deep vein thrombosis.

TABLE 5

LABORATORY AND COAGULATION DATA IN THE TWO TREATMENT GROUPS DURING THE STUDY (Means ± SD)

| | "CSA" Group (N = 22) | | | PLACEBO Group (N = 19) | | |
|---|---|---|---|---|---|---|
| | Week 4 | Week 10 | Week 14 | Week 4 | Week 10 | Week 14 |
| Fibrinogen (g/l) | 3.97 ± 0.71 | 3.71 ± 0.50 | 3.48 ± 0.47* | 3.50 ± 0.50 | 3.52 ± 0.55 | 3.34 ± 0.57 |
| Thrombin Clotting Time (% Normal) | 99.7 ± 5.32 | 102.8 ± 9.80 | 104.5 ± 10.76 | 97.2 ± 7.19 | 102 ± 11.10 | 99.3 ± 8.9 |
| Euglobin Lysis Time (secs) | 326.8 ± 14.03 | 331.1 ± 16.07 | 329.2 ± 13.64 | 334.4 ± 7.52 | 327.6 ± 8.15 | 328.5 ± 15.24 |
| Platelet Aggregation Time (secs) | 631.5 ± 7.63 | 638.5 ± 11.46 | 640.1 ± 10.84 | 646 ± 13.33 | 638.9 ± 12.34 | 637.5 ± 13.69 |
| Cephalin Time (secs) | 40.5 ± 4.8 | 40.5 ± 3.7 | 40.1 ± 2.9 | 39.5 ± 3.7 | 40.5 ± 3.0 | 41.1 ± 2.6 |
| Cholesterol (mg/dl) | 293.1 ± 13.6 | 290.8 ± 14.4 | 277.5 ± 17.7** | 291.0 ± 21.3 | 297.7 ± 11.9 | 288.3 ± 18.9 |
| 'S' Particles (mg/dl) | 532.6 ± 18.6 | 538.9 ± 20.9 | 536.5 ± 19.7 | 533.0 ± 17.1 | 537 ± 14.4 | 538.0 ± 16.1 |

Significant decrease vs. Baseline Values:
* $0.01 = P < 0.02$;
** $P < 0.01$

There were significant reductions in mean serum cholesterol concentrations and in mean fibrinogen levels in the "CSA" Group at Week 14 compared with baseline value. No other significant changes were recorded in any of the other measurements undertaken in the study.

"Active" CSA Tablets have been shown to give statistically significantly better results in patients with intermittent claudication than placebo, with considerable improvement in walking distance in those patients in receipt of "active" CSA. Orally administered "active" CSA was well tolerated and provoked no side effects of any significance.

140 patients undergoing either major gynaecological surgery or elective general surgical operations were investigated. Patients woh were undergoing surgery on the leg or on the hip were excluded from the study.

The following clinical data were obtained: age, weight, height, length of stay in hospital before operation, pre-operative haemoglobin levels, smoking habits, presence of varicose veins on clinical examination, history of venous thrombo-embolic disease, the nature of the operation, and whether surgery was for benign or malignant disease. Patients were stratified for age, sex and cigarette smoking status and were randomly allocated to a control (placebo) or active treatment group.

All patients received routine hospital physiotherapy before and after operation and were encouraged to become ambulant as soon as possible after operation.

The treatment group received by mouth "active" CSA 10 g throughout the two days preceding the operation, and thereafter 5 g "active" CSA (in divided dose) per day for seven days after operation or until the patient was discharged from hospital.

Platelets were measured with a Colter thrombocounter. Platelet factor III release was measured by the method of Spaet and Cintron, fibrinogen by the method of Ratnoff and Menzie and by electroimmunodiffusion, anti-thrombin III by the method of Howie et al., factor VIII by a one stage method of Brecken and Ratnoff, Euglobulin lysis time by the method of Nilsson and Olow, serum fibrin related antigen (FR antigen) by the method of Merskey et al., thrombin time by the method of Aylward et al., and platelet aggregation was measured to adenosene diphosphate, to collogen and to adrenaline by the aggregometer method of Bourne and Cross.

All patients underwent pre-operative isotopic scanning of the legs using the $^{125}$I-fibrinogen technique of Kakkar. Routine post-operative scanning was performed on the first, third and sixth days unless a significantly high count was obtained when daily scanning was started. The radioactive count in various positions on the legs was expressed as a direct percentage of the heart count. Patients were considered to have a deep vein thrombosis when an increase of 20% was observed at the same place on two different days or between two adjacent sites, provided this increase persisted for more than 24 hours.

There were 70 patients in the placebo group and 70 in the active treatment group. Clinical and coagulation data on the 140 patients before operation are shown in Table 6. The two groups were comparable in age distribution, sex ratio, and the types of operation performed. The incidence within both groups of the various factors that predispose to the development of deep vein thrombosis was comparable.

TABLE 6

Pre-operative clinical and coagulation data in the groups of patients investigated:

|  | Active Group: | Placebo Group: |
|---|---|---|
| Gynaecological Cases: | | |
| Number of cases | 32 | 32 |
| Age (years) | 52 ± 3 | 51 ± 2 |
| Cigarette Smokers (% of Group) | 35 | 37.5 |

TABLE 6-continued

Pre-operative clinical and coagulation data in the groups of patients investigated:

|  | Active Group: | Placebo Group: |
|---|---|---|
| Pre-Operative stay (days) | 4 ± 1 | 4 ± 1 |
| % Overweight for height | 12.5 | 15.6 |
| Presence of Varicose Veins (% Group) | 25 | 18.8 |
| Malignant Disease (% Group) | 6.25 | 6.25 |
| Fibrinogen (g/l) | 3.03 ± 0.11 | 2.99 ± 0.10 |
| Factor VII (% of Normal) | 116 ± 6 | 114 ± 7 |
| Euglobulin Lysis Time (mins) | 312 ± 21 | 326 ± 23 |
| Serum FR Antigen (mg/l) | 7 ± 1 | 8 ± 1 |
| Plasma Thrombin Clotting Time (% of normal) | 106 ± 4 | 104 ± 5 |
| General Surgical Cases: | | |
| Number of Cases | 38 | 38 |
| Age (years) | 42 ± 6 | 44 ± 3 |
| Female Cases | 12 | 13 |
| Cigarette Smoking (cases) | 13 | 14 |
| Pre-operative stay (days) | 2 ± 0.5 | 2 ± 0.5 |
| % overweight for height | 10 | 12.5 |
| Presence of Varicose Veins | 11 | 10 |
| Fibrinogen (g/l) | 2.94 ± 0.08 | 2.96 ± 0.09 |
| Factor VII (% of normal) | 123 ± 8 | 125 ± 7 |
| Euglobulin Lysis Time (mins) | 298 ± 15 | 296 ± 13 |
| Serum FR antigen (μg/l) | 8 ± 1 | 7 ± 1 |
| Plasma Thrombin Clotting time (% of normal) | 103 ± 4 | 102 ± 3 |

Table 7 shows the overall incidence of deep vein thrombosis in the placebo and treatment groups. Fifteen of the twenty-five patients with deep vein thrombosis in the placebo group and six of the eleven patients with deep vein thrombosis in the treatment group had positive bilateral leg scans. This is a significant difference (P<0.02). Consideration of the type of operation in the two groups of patients indicated a significant reduction in the incidence of deep vein thrombosis in the treated group particularly in those undergoing oopnorectomy. The incidence of deep vein thrombosis in both groups according to the type of operation is shown in Table 8.

TABLE 7

Incidence of Deep Vein Thrombosis in Both Groups of Patients

| Groups: | | No. Cases: | No. with Deep Vein Thombosis | No. of Bilateral Thrombosis |
|---|---|---|---|---|
| Gynaecological: | Control | 32 | 12(37.5%) | 8 |
|  | Treatment | 32 | 5(15.6%) | 3 |
| Gen. Surgical: | Control | 38 | 13(34.2%) | 7 |
|  | Treatment | 38 | 6(15.8%) | 3 |
| Total Patients | | 140 | 36(25.7%) | 21 |

TABLE 8

Incidence of Deep Vein Thrombosis in Both Groups of Patients According to Operative Procedure:

| | Placebo Group: | | Treated Group: | |
|---|---|---|---|---|
| Operation | No. (%) of Patients | No. (%) with Deep Vein Thrombosis | No. (%) of Patients | No. (5) with Deep Vein Thrombosis |
| Gynaecological | | | | |
| Abdominal Hysterectomy | 15(50%) | 5(15.6%) | 16(50%) | 2(6.3%) |
| Abdominal Hysterectomy and Oophorectomy | 9(28.1%) | 4(12.5%) | 10(31.2%) | 2(6.3%) |
| Bilateral Oophorectomy | 5(15.6%) | 2(6.3%) | 4(12.5%) | 1(3.1%) |
| Pelvic Floor Repair | 2(6.3%) | 1(3.1%) | 2(6.3%) | 0(0) |
| General Surgical | | | | |
| Laparotomy | 16(42.1%) | 8(21.1%) | 14(36.8%) | 2(5.3%) |

TABLE 8-continued

Incidence of Deep Vein Thrombosis in Both Groups of Patients According to Operative Procedure:

| Operation | Placebo Group: | | Treated Group: | |
| --- | --- | --- | --- | --- |
| | No. (%) of Patients | No. (%) with Deep Vein Thrombosis | No. (%) of Patients | No. (5) with Deep Vein Thrombosis |
| Mastectomy | 9(23.7%) | 4(10.5%) | 10(26.3%) | 2(5.3%) |
| Adrenalactomy | 10(26.3%) | 1(2.6%) | 9(23.7%) | 1(2.6%) |
| Miscellaneous | 3(7.9%) | 0(0) | 5(13.2%) | 1(2.6%) |

Excessive blood loss during or after operation was not a problem in any patient in either the treated or control group.

Platelet aggregation time was markedly increased in patients on "active" CSA. There was no difference in the platelet count in the two groups, nor a significant change in the haematocrit.

The introduction of the radioactive fibrogen test has revealed the magnitude of the problem presented by post-operative deep vein thrombosis and correlation with phlebography has confirmed that this test is an accurate and quick method for assessing the incidence and site of thrombi in post-operative patients.

In general surgical patients, thrombi usually start in the deep sinuses of the calf and if the thrombosis is limited to these veins and the deep tibial veins the risk of pulmonary embolism is low. However, extension of the thrombus into the popliteal and lower femoral veins increase the risk of pulmonary embolism. It is therefore of paramount importance to prevent post-operative deep vein thrombosis whenever possible and limit propogation should a calf thrombus develop.

These results indicate that "active" CSA decreases the incidence of post-operative deep vein thrombosis as detected by the radioactive fibrinogen test in general surgical patients and in gynaecological patients. There were no evident complications from the administration of the drug. Testing platelet function and the effects of various drugs in-vitro may no reflect the in-vivo situation. Nevertheless such tests serve as monitors and confirmed that patients were receiving active treatment. It is not possible to state here, from the results obtained, the possible modes of action of "active" CSA although it is possible that inhibition of platelet aggregation and prolongation of plasma thrombin clotting time are involved. However, it should be noted that "active" CSA has also been shown to reduce elevated levels of plasma fibrinogen and this observation may be of significance to the beneficial effect of "active" CSA.

Having fully described the invention, it is intended that it be limited only by the lawful scope of the appended claims.

I claim:

1. In an improved process or method for the preparation of pharmaceutical grade biologically "active" chondroitin sulfate, predominantly condroitin sulfate A, chondroitin sulfate C, and mixtures thereof from source material comprising forming a solution from the source material containing said "active" material, the improvement comprising adding thereto a complexing agent selected from the group consisting of cetyl pyridinium chloride, a quarternary ammonium salt and an anion exchange resin to form a precipitate which is a water insoluble complex of the active material and the complexing agent, and breaking said complex to recover the pharmaceutical grade "active" material.

2. The method of claim 1 wherein the source material is first defatted.

3. The method of claim 1 wherein the source material is first defatted and ground.

4. The method of claim 1 wherein the complex is broken by a base or hypertonic saline.

5. The method of claim 1 wherein the quaternary ammonium salt is an n-alkyl dimethyl benzyl ammonium chloride.

6. The method of claim 1 wherein the anion exchange resin is a crosslinked benzene-divinylbenzene copolymer containing lower alkyl quaternary amine groups.

7. A water-insoluble complex of an "active" CSA and/or CSC and a complexing agent selected from the group consisting of cetyl pyridinium chloride, a quaternary ammonium salt and an anion exchange resin.

8. The complex of claim 7 wherein the complexing agent is cetyl pyridinium chloride.

9. The complex of claim 7 wherein the quaternary ammonium salt is an n-alkyl dimethyl benzyl ammonium chloride.

10. The complex of claim 7 wherein the anion exchange resin is a crosslinked benzene-divinylbenzene copolymer containing lower alkyl quaternary amine groups.

* * * * *